United States Patent [19]
Emanuel et al.

[11] Patent Number: 5,576,178
[45] Date of Patent: Nov. 19, 1996

[54] METHOD OF DETECTING GENETIC DELETIONS AND MUTATIONS ASSOCIATED WITH DIGEORGE SYNDROME, VELOCARDIOFACIAL SYNDROME, CHARGE ASSOCIATION, CONOTRUNCAL CARDIAC DEFECT, AND CLEFT PALATE AND PROBES USEFUL THEREFOR

[75] Inventors: Beverly S. Emanuel, Broomall; Marcia L. Budarf, Moylan; Deborah Driscoll, Wynnewood, all of Pa.

[73] Assignees: The Childrens Hospital of Philadelphia; The Trustees of the University of Pennsylvania, both of Philadelphia, Pa.

[21] Appl. No.: 156,672

[22] Filed: Nov. 22, 1993

Related U.S. Application Data

[63] Continuation of Ser. No. 911,534, Jul. 10, 1992, abandoned, which is a continuation-in-part of Ser. No. 770,758, Oct. 4, 1991, abandoned.

[51] Int. Cl.[6] .............................. C12Q 1/68; C12P 19/34; C07H 21/02; C07H 21/04
[52] U.S. Cl. ......................... 435/6; 435/91.2; 536/24.31
[58] Field of Search ....................... 435/6, 91.2; 935/77, 935/78; 536/24.31, 24.33; 436/811, 813

[56] References Cited

U.S. PATENT DOCUMENTS 4,683,195   7/1987   Mullis et al. ............................. 435/6

OTHER PUBLICATIONS

Stevens et al., Pediatrics 85: 526–530 (1990) "DiGeorge anomaly and Velocardiofacial Syndrome".
Scrambler et al., Genomics 10:201–206 (1991) "Microdeletions within 22q11 associated with ...".
De La Chapelle et al., Hum. Genet 57(3): 253–256 (1981) "A deletion in Chromosome 22 can cause ...".
Fibison et al., Am. J. Hum. Genet. 46:888–895 (1990) "Molecular Studies of DiGeorge Syndrome".
Litt. et al., P.N.A.S. 82:6206–6210 (1985) "A highly polymophic locus in human DNA ...".
Budarf. et al., Genomics 10:1–7 (1991) "Isolation and Regional Localization of 35 ...".
Augusseau et al., "DiGeorge Syndrome and 22q11 Rearrangements", *Human Genet.* 74:206 (1986).
Back et al., "Partial Monosomy 22pter→q11 in a Newborn with the Clinical Features of Trisomy 13 Syndrome" *Ann. Genet.* 23: 244–288 (1980).

(List continued on next page.)

*Primary Examiner*—Stephanie W. Zitomer
*Assistant Examiner*—Eggerton Campbell
*Attorney, Agent, or Firm*—Woodcock Washburn Kurtz Mackiewicz & Norris

[57] ABSTRACT

There is provided by this invention methods of detecting genetic deletions and mutations associated with at least one condition selected from the group consisting of DiGeorge syndrome, Velocardiofacial syndrome, CHARGE association, conotruncal cardiac defect, and cleft palate in a human patient comprising the steps of providing a DNA containing test sample from said human patient; identifying whether there are less than two functional copies of the DiGeorge syndrome critical region loci, whereby said identification of less than two copies of the DiGeorge syndrome critical region loci is indicative of a likelihood that said person has at least one of DiGeorge syndrome, Velocardiofacial syndrome, CHARGE association, conotruncal cardiac defect, and cleft palate. Probes and primers useful in the invention are also provided as are diagnostic kits.

6 Claims, 1 Drawing Sheet

OTHER PUBLICATIONS

Bowen et al., "Thymus Deficiency in an Infant with a Chromosome t(18;22) (q12.2;p11.2)pat Rearrangment", *Clin. Genet.* 29: 174–177 (1986).

Budarf et al., "Short Communication: Linear Order of the Four BCR–Related Loci in 22q11", *Genomics* 3: 168–171 (1991).

Budarf et al., "Isolation and Regional Localization of 35 Unique Anonymous DNA Markers for Human Chromosome 22", *Genomics* 10: 996–1002 (1991).

Carey, J. C., "Spectrum of the DiGeorge Syndrome" *J. Pediatrics*, 96: 955–956 (1980).

Croce et al., "Mapping of Four Distinct BCR–Related Loci to Chromosome Region 22q11: Order of BCR Loci Relative to Chronic Myelogenous Leukemia and Acute Lymphoblastic Leukemia Breakpoints", *Proc. Natl. Acad. Sci.* 84: 7174–7178 (1987).

Dobyns et al., "Miller–Dieker Syndrome: Lissencephaly and Monosomy 17p", *J. Pediatr* 102: 552–558 (1983).

Donis–Keller et al., "A Genetic Linkage Map of the Human Genome", *Cell* 51: 319–337 (1987).

Driscoll et al, "A Genetic Etiology for DiGeorge Syndrome: Consistent Deletions and Microdeletions of 22q11", *Am J. Human Genet.* 50: 924–933 (1992).

Driscoll et al, "Antenatal Diagnosis of DiGeorge Syndrome" *Lancet* 338: 1390–1391 (1991).

Driscoll, et al., "Molecular Analysis of DiGeorge Syndrome: 22q11 Interstitial Deletions", *Am. J. Hum. Genet* 47(3): A215 (1990).

El–Fouley et al. "DiGeorge Anomaly in an Infant with Deletion of Chromosome 22 and Dup(9p) Due to Adjacent Type II Disjunction", *Am. J. Med. Genet* 38: 569–578 (1991).

Faed, et al., "Features of Di George Syndrome in a Child with 45, XX, –3, –22, +der(3), t(3;22) (p25;q11)", *J. Med/Genet* 24: 225–234 (1987).

Feinberg and Vogelstein, "ADDENDUM: A Technique for Radiolabeling DNA Restriction Endonuclease Fragments to High Specific Activity", *Anal. Biochem.* 137: 266–267 (1984).

Fibison, et al. "A Genetic map of 22q11 and Its Application to the Study of DiGeorge Syndrome", *Am. J. Hum. Genet* 47(3): A178 (1990).

Goldberg et al., "Phenotypic Overlap Between Velo–Cardio–Facial Syndrome (VCF) and the DiGeorge Sequence (DGS)", *Am. J. Hum. Genet.* 37: A54 (1985).

Greenberg et al. "Cytogenetic Findings in a Prospective Series of Patients with DiGeorge Anomaly", *Am. J. Hum. Genet.* 43: 605–611 (1988).

Greenberg et al., "Familial DiGeorge Syndrome and Associated Partial Monosomy of Chromosome 22", *Human Genet.* 65: 317–319 (1984).

Kelley, et al. "The Association of the DiGeorge Anomalad with Partial Monosomy of Chromosome 22", *J. Pediatr.* 101: 197–200 (1982).

Knoll et al., "Angelman and Prader–Willi Syndromes Share a Common Chromosome 15 Deletion but Differ in Parental Origin of the Deletion", *Am. Med. Genet.* 32: 285–290 (1989).

Kuwano et al., "Detection of Deletions and Cryptic Translocations in Miller–Dieker Syndrome by In Situ Hybridization", *Am. J. Human Genetics*, 49: 707–714 (1991).

Lammer and Opitz, "DiGeorge Anomaly as a Developmental Field Defect", *Am. J. Med. Genet. Supp.* 2: 113–127 (1986).

Langer et al. "The Tricho–Rhino–Phalangeal Syndrome with Exostoses (or Langer–Giedion Syndrome): Four Additional Patients Without Mental Retardation and Review of the Literature", *Am. J. Med. Genet.* 19: 81–111 (1984).

Ledbetter et al. "Chromosome 15 Abnormalities and the Prader–Willi Syndrome: A Follow–up Report of 40 Cases", *Am. J. Hum. Genet.* 34: 278–285 (1982).

Lele et al. "Chromosome Deletion in a Case of Retinoblastoma", *Ann. Hum. Genet* 27: 171–174 (1963).

Mascarello et al., "Interstitial Deletion of Chromosome 22 in a Patient with DiGeorge Malformation Sequence", *Am. J. Med. Genet* 32: 112–114 (1989).

McDermid et al., "Toward a Long–Range Map of Human Chromosomal Band 22q11", *Genomics* 5: 1–8 (1989).

McDermid et al., "Characterization of the Supernumerary Chromosome in Cat Eye Syndrome", *Science* 232:646–648 (1986).

Pivnick et al., "Adjacent–2 Disjunction of a Maternal t(9;22) Leading to Duplication 9pter→q22 and Deficiency of 22pter→q11.2", *Am. J. Med. Genet.* 37: 92–96 (1990).

Riccardi et al, "Chromosomal Imbalance in the Aniridia–Wilms' Tumor Association: 11p Interstitial Deletion", *Pediatrics* 61: 604–610 (1978).

Rouleau et al., "A Genetic Linkage Map of the Long Arm of Human Chromosome 22", *Genomics* 4:1–6 (1989).

Schinzel "Microdeletion Syndromes, Balanced Translocations, and Gene Mapping", *J. Med. Genet*, 5: 454–462 (1988).

Schmickel, "Contiguous Gene Syndromes: A Component of Recognizable Syndromes", *J. Pediatr.* 109: 231–241 (1986).

Shprintzen, et al. "The Velo–Cardio–Facial Syndrome: A Clinical and Genetic Analysis" *Pediatr.* 67: 167–172 (1981).

Shprintzen et al. "A New Syndrome Involving Cleft Palate, Cardiac Anomalies, Typical Facies, and Learning Disabilities: Velo–Cardio–Facial Syndrome", *Cleft Palate J.* 15: 56–62 (1978).

Shprintzen et al. et, "The Expanded Velo–Cardio–Facial Syndrome (VCF): Additional Features of the Most Common Clefting Syndrome" *Am. J. Human Genet.* 37: A77 (1985).

Southern, "Detection of Specific Sequences Among DNA Fragments Separated by Gel Electrophoresis", *J. Mol. Biol.* 98: 503–517 (1975).

Stratton et al., "New Chromosomal Syndrome: Miller–Dieker Syndrome and Monosomy 17p13", *Human Genet* 67: 193–200 (1984).

Williams et al. "Male–to–Male Transmission of the Velo–Cardio–Facial Syndrome: A Case Report and Review of 60 Cases", *J. Craniofacial Genet* 5: 175–180 (1985).

Bostein et al., "Construction of a Genetic Linkage Map in Man Using Restriction Fragment Length Polymorphisms", *Am J Hum Genet* vol. 32 No. 3, 314–331 (1980).

METHOD OF DETECTING GENETIC DELETIONS AND MUTATIONS ASSOCIATED WITH DIGEORGE SYNDROME, VELOCARDIOFACIAL SYNDROME, CHARGE ASSOCIATION, CONOTRUNCAL CARDIAC DEFECT, AND CLEFT PALATE AND PROBES USEFUL THEREFOR

REFERENCE TO GOVERNMENT GRANTS

The work present herein was supported in part by National Institute of Health grants CA 39926, HG00425, and HD26979 and from the Reproductive Scientist Training Program (D.A.D.). The United States government has certain rights in the invention.

CROSS REFERENCE TO RELATED APPLICATIONS

This is a continuation of application Ser. No. 07/911,534, filed Jul. 10, 1992 now abandoned, which is a continuation-in-part of Ser. No. 07/770,758, filed Oct. 4, 1991 now abandoned.

FIELD OF THE INVENTION

The present invention relates to the field of human diagnostics. More particularly, the invention relates to the detection of genetic deletions and mutations associated with DiGeorge Syndrome (DGS) and related syndromes of Velocardiofacial (Shprintzen) syndrome, CHARGE association, conotruncal cardiac defect, and cleft palate in humans using probes within the common region of overlap for substantially all deletions and mutations associated with these diseases.

BACKGROUND OF THE INVENTION

DiGeorge syndrome (DGS) is a developmental field defect of the third and fourth pharyngeal pouches characterized by thymic aplasia or hypoplasia, absent or hypoplastic parathyroid glands and conotruncal cardiac malformations. The etiology is presumed to be heterogenous with reported cases demonstrating autosomal dominant, autosomal recessive, X-linked and chromosomal modes of inheritance (Lammer and Opitz, (1986) Am J. Med. Genet. 2:113–127). Approximately 15–20% of patients with DGS have detectable chromosomal abnormalities (Greenberg, et al. (1988) Am. J. Hum. Genet. 43: 605–611). There are several examples of specific associations between chromosomal deletions and diseases, including Prader-Willi syndrome (Ledbetter et al. (1982) Am. J. Hum. Genet. 34: 278–285), Laner -Gideon syndrome (Langer et al. (1984), Am. J. Med. Genet. 19: 81–111), Miller-Dieker syndrome (Dobyns et al., (1983), J. Pediatr 102: 552–558; Stratton et al., (1984), Human Genet 67: 193–200) the aniridia-Wilms tumor association (Riccardi et al, (1978), Pediatrics 61: 604–610), and retinoblastoma (Lele et al. (1963), Ann. Hum Genet 27: 171–174). DiGeorge syndrome has been linked to chromosomal deletion of chromosome 22. All of these syndromes have been analyzed using molecular techniques (reviewed by Schinzel (1988), J. Med. Genet, 5: 454–462). DGS has many of the characteristics associated with this group of deletions syndromes, which have been referred to by Schmickel (1986), J. Pediatr. 109: 231–241, as "contiguous gene syndromes". These syndromes tend to be rare, are often sporadic, and have few examples where the disorder is familial. Patients show variation in the severity of their associated symptoms and often manifest additional phenotypic features, possible reflective of the number of genes involved.

The majority of cytogenetically abnormal cases of DGS reported involved chromosome 22 and result from malsegregation of a familial balanced translocation leading to monosomy 22pter→22q11 (Back et al. (1980), Ann. Genet. 23: 244–288; de la Chapelle et al. (1981), Hum Genet. 57: 253– 256; Kelley, et al. (1982) J. Pediatr. 101: 197–200 (1982); Greenberg et al., (1984), Human Genet. 65: 317–319; Greenberg et al. (1988) Am. J. Hum. Genet. 43: 605–611; Augusseau, et al. (1986) Hum. Genet 74: 206; Bowen et al., (1986), Clin. Genet. 29: 174–177; Faed, et al. (1987), J. Med/Genet 24: 225–234 (1987). Two patients have been reported with interstitial deletions, del(22)(q11.21→q11.23) (Greenberg et al. (1988), Am. J. Human Genet 43: 605–611; Mascarello et al. (1989), Am. J. Med. Genet 32: 112–114; El-Fouley et al. (1991), Am J. Med. Genet 38: 569–578 and Driscoll, et al. (1992), Am. J. Hum Genet. 50: 924–933. Based on cytogenetic studies, it has been hypothesized that the deletion of contiguous genes located on chromosome 22 results in DGS and that the region critical to DGS (DGCR) lies in 22q11. (de la Chapelle et al., (1981), Hum. Genet 57:253–256; Kelley et al., (1982), J. Pediatr. 101: 197–200; Schmickel, (1986), J. Pediatr. 109: 231–241). The description of a DGS-associated region within 22q11 which invariably involves codeletion of loci D22S75, D22S66 and D22S259 has begun to delineate the DiGeorge syndrome chromosome region (DGCR) (Driscoll et al (1992), Am J. Human Genet. 50: 924–933.

Velo-cardio-facial syndrome (VCF) is an autosomal dominant disorder characterized by cleft palate, cardiac defects, learning disabilities and a typical facial dysmorphism (Shprintzen et al. (1978), Cleft Palate J. 15: 56; Spprintzen et al. (1981), Pediatr. 67: 167–172 and Williams et al. (1985), J. Craniofacial Genet 5: 175–180). Additional features have been described including microcephaly, short stature, inguinal and umbilical hernias, Robin sequence, scoliosis, platybasia, opthalmologic abnormalities, neonatal hypocalcemia and decreased lymphoid tissue (Shprintzen et al. (1985), Am J. Human Genet 37: A77; Williams et al, (1985), J. Craniofacial Genet. 5: 175–180). The presence of neonatal hypocalcemia, absent or hypoplastic lymphoid tissue and T-cell dysfunction, which are features of DiGeorge syndrome (DGS), suggests that DGS and VCF may share a common pathogenesis (Goldberg et al. (1985), Am. J. Hum. Genet. 37: A54). Review of previously reported DGS cases with autosomal dominant transmission suggests that these families actually have clinical features more consistent with the diagnosis of VCF (Lammer and Opitz, (1986), Am. J. Med. Genet. 29: 113–127; Stevens et al. (1990), Pediatrics 85: 526–530. Based on the phenotypic overlap between DGS and VCF, it is believed that VCF could be caused by deletion of genes from within the DGCR or from a partially overlapping region.

CHARGE association and conotruncal cardiac defect are conditions in which the abnormalities that constitute DGS also play a significant role.

Even high resolution cytogenetic studies are not always adequate to detect genetic deletions associated with conditions such as DGS, VCF and related conditions such as CHARGE association, conotruncal defect, and cleft palate. In many cases deletions within chromosome 22 are molecular deletions which may only be detected by means of molecular studies. Large molecular deletions can be detected for example, by restriction fragment length polymorphism (RFLP) analysis using several anonymous DNA markers located within the DGCR. However, RFLP studies are not always fully informative. In the past, studies of uninformative patients involved segregation of maternal and paternal homologs of chromosome 22 into different somatic cell hybrids. However, the construction of somatic cell hybrids is labor intensive and is not practical as a routine diagnostic tool. A fast and efficient method for detecting conditions associated with deletions on chromsome 22 such as DGS, VCF, CHARGE association, conotruncal defect, and cleft palate is greatly needed.

Probes to deletion regions have been used diagnostically. For example, fluorescence in situ hybridization (FISH) utilizing cosmid probes from the 17p13.3 region has been used to identify submicroscopic deletions and to define cryptic translocations in patients with Miller-Dieker syndrome (Kuwano et al. (1991), Am J. Human Genetics, 49: 707–714).

Therefore, probes directed to the DiGeorge syndrome critical region are greatly desired to enhance the detection of genetic deletions and mutations associated with DiGeorge syndrome and the related conditions of Velocardiofacial syndrome, CHARGE association, conotruncal cardiac defect and cleft palate. Diagnosis of a deletion or mutation will permit the clinician to provide the proband as well as the family with an accurate assessment of the recurrence risk and to offer prenatal monitoring for the detection of a deletion in subsequent pregnancies. In addition to the use of ultrasonography and fetal echocardiography for the detection of cleft palate and congenital heart defects, amniocentesis or chorionic villus sampling can be utilized for the cytogenetic, fluorescence in situ hybridization (FISH) and molecular evaluation of the fetus for 22q11 deletions and mutations (Driscoll et al (1991) Lancet 338: 1390–1391).

SUMMARY OF THE INVENTION

There is provided by this invention novel methods of detecting genetic deletions and mutations associated with at least one condition selected from the group consisting of DiGeorge syndrome, Velocardiofacial syndrome, CHARGE association, conotruncal cardiac defect, and cleft palate in a human patient. The method comprising the steps of providing a DNA containing test sample from said human patient; identifying whether there are less than two functional copies of the DiGeorge syndrome critical region loci, whereby said identification of less than two functional copies of the DiGeorge syndrome critical region loci is indicative of a likelihood that said person has a genetic deletion or mutation associated with at least one condition selected from the group consisting of DiGeorge syndrome, Velocardiofacial syndrome, CHARGE association, conotruncal cardiac defect and cleft palate.

In another aspect of the invention there is provided novel methods of preparing diagnostic probes useful for the detection of genetic deletions and mutations associated with at least one condition selected from the group consisting of DiGeorge Syndrome, Velocardiofacial syndrome, CHARGE association, conotruncal cardiac defect, and cleft palate. The invention comprises the steps of preparing primer pairs effective to amplify a region of chromosome 22q11 shown to be unique sequences in the DiGeorge syndrome critical region; synthesizing DNA substantially complementary to a region of normal human genomic DNA or cDNA by PCR amplification using said primer pairs; and isolating a DiGeorge syndrome critical region probe from a library containing human chromosome 22 using said substantially complementary DNA. In preferred embodiments the primers are selected from the group consisting of 5'ACACTGGTC-CACAGTGCCAG3' (SEQ ID NO: 1) and 5'TGT-GAGGGCTTGCTCTGAGC3' (SEQ ID NO: 2); 5'TGG-TACCGCTGCTCAGAGGGC3' (SEQ ID NO: 3) and 5'TCCCAGCCTCTGGCCTGAGTG3' (SEQ ID NO: 4); and 5'CTAACACCTATCCTCCGCCG3' (SEQ ID NO: 5) and 5'GGCAGCAGGGAAACAGAAAC3' (SEQ ID NO: 6). Also provided by the invention are the probes produced thereby.

In yet another aspect of the invention there is provided novel diagnostic probes useful for the detection genetic deletions and mutations associated with at least one condition selected from the group consisting of DiGeorge syndrome, Velocardiofacial syndrome, CHARGE association, conotruncal cardiac defect and cleft palate. These methods comprise PCR amplifying a clone from a library containing chromosome 22 to identify clones containing the probe. Also provided by the invention are the probes produced thereby.

There is further provided by the invention diagnostic kits for the detection of a genetic deletion associated with at least one condition selected from the group consisting of DiGeorge syndrome, Velocardiofacial syndrome, CHARGE association, conotruncal cardiac defect and cleft palate comprising a diagnostic probe selected from the group consisting of probes prepared by methods of this invention or primer pairs effective to amplify a region of chromosome 22q11 shown to be unique sequences in the DiGeorge syndrome critical region.

These and other aspects of the invention will become more apparent from the following detailed description when taken in conjunction with the following drawing.

DETAILED DESCRIPTION OF THE INVENTION

Figure 1:
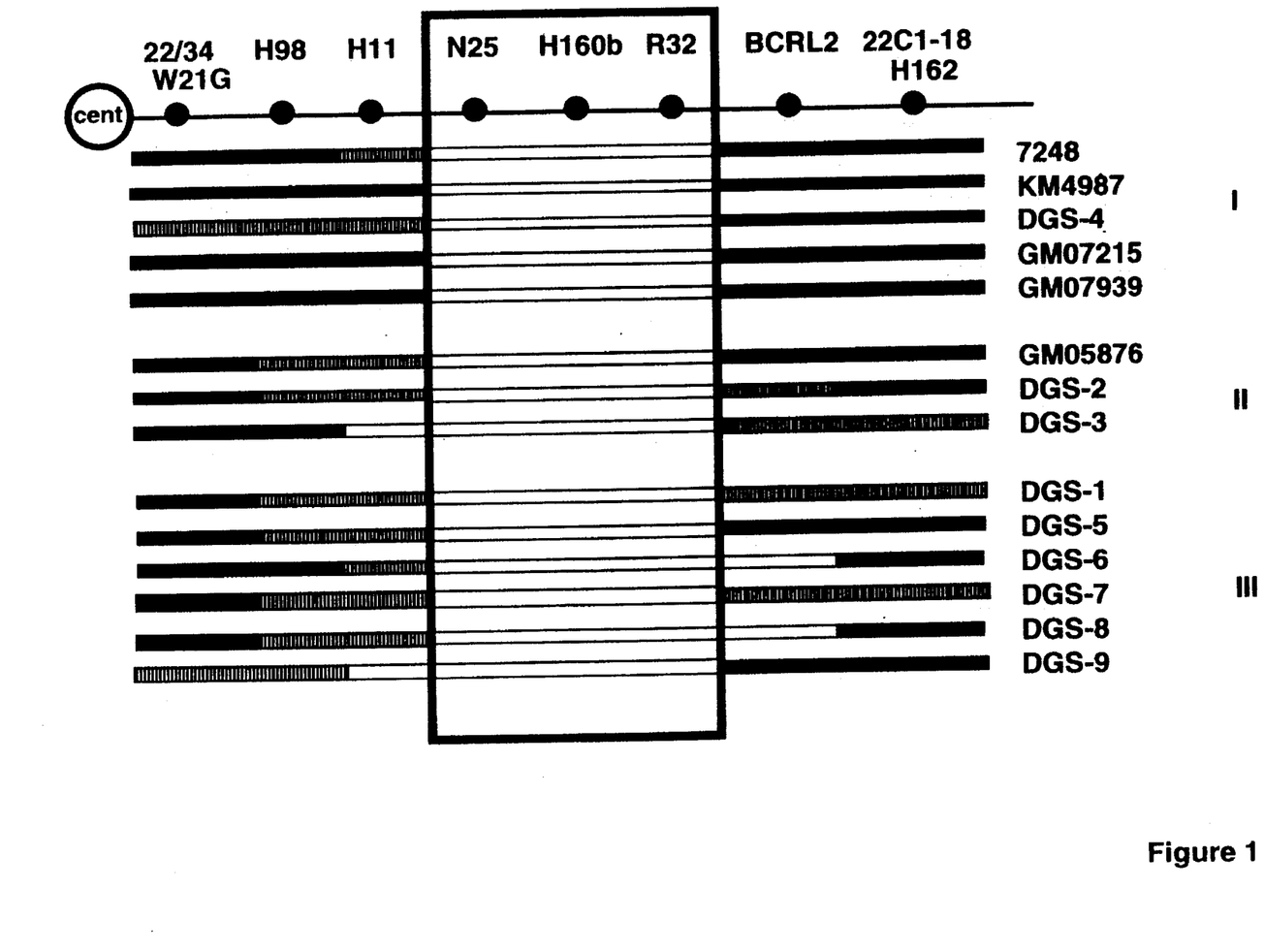
FIG. 1 is a graphic representation of RFLP and dosage studies of fourteen DGS probands, grouped according to cytogenetic findings. "I" represents del(22)(q11.21q11.23), "II" represents possible deletion of 22q11; "III" represents normal karyotype. Probes are ordered from centromere (cent) to telomere (right). The bars represent results of hybridization studies; fully shaded bars represent the presence of two copies of the locus; hatched bars represent uninformative or non-polymorphic loci for which dosage has not been performed to determine copy number; open bars represent deletions (singe allele). The minimal region of overlap is indicated by the box and includes probes N25, pH160b and pR32.

What is meant by the "DiGeorge Syndrome Critical Region (DGCR)" as used herein refers to the region on chromosome 22 as shown in the boxed region of FIG. 1. It is believed the region spanning from N25 to R32 is approximately 1.5 megabases. The DGCR does not include the chromosome loci recognized by the probe Hll(D22S36) or the loci recognized by probe BCRL2, however the DGCR is believed to extend at least about 0.5 megabases on either side of the loci recognized by probes N25 and R32.

Cytogenetic and molecular studies have lead to the partial characterization of the DiGeorge syndrome critical region located on chromosome 22q11. Molecular studies of the two aforementioned interstitial deletion probands demonstrated that loci D22S9 and D22S43 flank the critical region proximally. Loss of an allele at a more distal locus, BCRL2, was demonstrated in one of these probands suggesting that the distal boundary for the DGS critical region is in proximity to the BCRL2 locus (Fibison et al. (1990). In a more recent study, markers, KI-506, KI-197 and KI-716 were proposed as flanking markers. In addition, DNA microdeletions were demonstrated in two probands whose karyotype was normal upon routine cytogenic analysis at the 400 band stage of resolution (Scambler et al. (1991), *Genomics,* 10: 201–206).

Studies of DGS probands based upon cytogenetic evidence of a deletion within chromosome band 22q11 and normal karyotype by routine chromosomal analysis support the presence of a DGS critical region within 22q11 (Fibison, et al. (1990), *Am. J. Hum. Genet* 47(3): A178, Driscoll, et al., (1990), *Am. J. Hum. Genet* 47(3): A215, Scambler, et al., (1991), *Genomics* 10: 201–206). Greater understanding of DGS and the critical region associated with DiGeorge syndrome, DGCR, have lead to new and better methods of diagnosis. For example, fluorescence in situ hybridization utilizing cosmid clones containing probes such as N25, pH160 and R32, which are derived from the DGS critical region can be used to diagnose DGS and the related syndromes of Velocardiofacial syndrome, CHARGE association, conotruncal cardiac defect, and cleft palate. Table 7 sets out probes referred to herein as well as the loci to which they correspond. In some cases, reference to loci may be accompanied by a corresponding parenthesized reference to a probe directed to said loci.

TABLE 7

| D#/ Lab name | Insert (kB) | Vector | Location |
| --- | --- | --- | --- |
| D22S75/N25 | 20.0 | NotI/EMBL4N | 22q11 |
| D22S259/pR32 | 7.0 | RI/SK+ | 22q11 |
| D22S66/pH160b | 3.0 | Hd3/pUC18 | 22q11 |
| D22S57/pH98 | 0.7 | Hd3/pUC18 | 22q11 |
| D22S36/pH11 | 1.0 | Hd3/pUC18 | 22q11 |
| D22S68/pH162 | 5.0 | Hd3/pUC18 | 22q11 |

Two loci have been identified, D22S75 (N25) and D22S259 (pR32), that are deleted in fourteen of fourteen DGS probands, eight with either cytogenetically visible deletions or possible deletions within 22q11 and six cytogenetically normal probands. In addition, deletions of D22S66 (pH160b) have been demonstrated in eight of eight probands studied including three with normal karyotypes. It is believed that this locus is deleted in the remaining six probands based on its location between D22S75 and D22S259, both of which are consistently deleted in these fourteen DGS probands. De novo deletion of loci in the DGS critical region has also been demonstrated by RFLP analysis. The presence of a DGS critical deleted region and a minimal region of overlap have been established. Based on preliminary pulsed field gel electrophoresis data the size of the region is estimated to be approximately 0.75 megabase.

Although hemizygous DGS probands at proximal locus D22536 (pH11) have been identified using RFLP analysis, the demonstration of heterozygous probands excludes this locus from the minimal critical region. Dosage studies of DGS probands demonstrate that the more distal BCRL2 locus is not consistently deleted in DG5. Therefore, it has been concluded that D22S36, proximally, and BCRL2, distally, flank the critical region.

The origin of the de novo deletions was established by RFLP analysis of five informative families. Four of five probands failed to inherit a maternal allele; one proband did not inherit a paternal allele. Based on this data and reports of both maternally and paternally inherited translocations in DG5 patients there does not appear to be a consistent parent of origin or imprinting effect (de la Chapelle et al., (1981), *Hum. Genet.* 57: 253–256; Kelley et al., (1982), *J. Pediatr.* 101: 197–200; Greenberg et al., (1984), *Human Genet.,* 65: 317–319; Augusseau et al., (1986), *Human Genet.* 74:206; Bowen et al., (1986), *Clin. Genet.* 29: 174–177; Pivnick et al., (1990), *Am. J. Med. Genet.* 37: 92–96; El-Fouly et al., (1990), *Am. J. Med. Genet.* 38: 569–578). This is in contrast to what has been observed in other microdeletion syndromes such as Prader-Willi and Angelman syndromes where paternal and maternal deletions, respectively, are the rule (Knoll et al., (1989), *Am. J. Med. Genet.* 32: 285–290).

There are several features of chromosome 22 which might account for the various patterns of inheritance observed in association with DGS. These include its high recombination rate, acrocentric morphology and frequent involvement in translocations. There is evidence for a high rate of recombination in the proximal region of 22q11 from meiotic mapping studies (Fibison et al., (1990), *Am. J. Hum. Genet.* 47(3):A178; Fibison et al., submitted). This could produce de novo 22q11 interstitial deletions, accounting for the sporadic cases of DGS. Dosage analysis with pR32 (D22S259) demonstrated loss of an allele in a DGS-affected offspring (DGS-7) of D22S259 heterozygous parents. These results are consistent with a de novo deletion in the proband which presumably arose during meiosis, perhaps as a result of recombination. Gonadal mosaicism, although rare, could give rise to affected siblings.

Balanced translocations between the proximal long arms of acrocentric chromosomes might account for some cases of DGS. During meiosis, all five pairs of acrocentric chromosomes coalesce around the nucleolus. It has been suggested that Robertsonian translocations occur at this time. Balanced translocations between the proximal long arms of the acrocentric chromosomes might also occur at this stage of meiosis. Malsegregation of a translocation with breakpoints in 22q11 and the q11 region of any of the other acrocentric chromosome could produce 22pter→q11 monosomy and trisomy for pter→q11 of the other involved acrocentric which might remain undetected upon standard cytogenetic analysis. Malsegregation of such cryptic balanced translocations could produce DGS affected siblings in families, whereas trisomy for the other involved acrocentric autosome could explain the phenotypic variability seen between DGS patients.

It has been observed that, amongst constitutional chromosomal abnormalities, a greater than expected number of visible translocations involve chromosomal band 22q11 (Yu et al., 1978). These findings support schemes presented for generating familial DGS cases. Investigation of these DGS-generating mechanisms is facilitated by fluorescence in situ hybridization analysis of DGS patients and their parents using centromere-specific probes for each of the acrocentric chromosomes, together with hybridization probes to the DGS critical region provided by the present invention.

All fourteen DGS cases studied have either cytogenetically visible deletions utilizing high resolution banding techniques or submicroscopic deletions detected by molecular analysis with probes from 22q11. This strongly supports a systematic approach for the detection of deletions in DGS which combines both high resolution cytogenetic analysis and molecular analysis with probes for the critical region. Chromosomal analysis may detect translocations or cytogenetic abnormalities of chromosomes other than 22 however, results suggest that molecular studies may actually be more sensitive than high resolution cytogenetic analysis for the detection of small interstitial deletions. These deletions are quite difficult to visualize in this small, primarily euchromatic chromosome. Hence, chromosome 22 specific cosmids for the loci identified in the critical region should prove to be useful reagents for the rapid detection of microdeletions in the diagnosis of DGS.

Smaller interstitial deletions are believed to produce a less severe phenotype, for example the phenotype associated with the so-called partial DiGeorge syndrome. Reproduction for less severely affected patients might not be compromised and DGS associated with a deletion could appear to segregate, at least in some cases, as an autosomal dominant disorder. In support of this hypothesis deletions of loci within the DGS critical region have been demonstrated in a mother and child with Velocardiofacial syndrome, an autosomal dominant disorder often associated with features of DGS (unpublished results; Shprintzen et al.,et, (1985), *Am. J. Human Genet.* 37: A77; Goldberg et al., (1985), *Am. J. Hum. Genet.* 37: A54; Stevens et al., (1990), *Pediatrics* 85: 526–530). Identified deletions in this region may account for the overlapping phenotypic features between DGS and Velocardiofacial syndrome. Fourteen of 15 VCF patients studies have either cytogenetically visible interstitial deletions of 22q11.2 or submicroscopic deletions of DNA within the DGCR. These 14 patients have deletions of both the most proximal marker (N25) and distal marker (pR32) in the DGCR. This would account for the overlapping phenotypic features observed in VCF and DGS. At this time, molecular differences have not been identified to explain the phenotypic variability among VCF patients or between these two groups of patients. Preliminary studies of the DGCR suggest that this region is large (greater than 750 kb) and contains several genes (Driscoll et al. (1992), *Am. J. Hum. Genet.* 50: 924–933 (1992). It is believed that in some cases deletions or mutations of different loci within 22q11 may correlate with the presence of individual clinical features such as cleft palate, cardiac defect and thymic hypoplasia or aplasia. However, phenotypic differences between patients or within families may result from differences in genetic background as well as intra-uterine environment.

This is the first study to demonstrate failure to inherit a 22q11 allele in a VCF proband by RFLP analysis of both the affected parent and child (VCF-4/VCF-5 and VCF-10/VCF-11). In these families, hemizygosity at D22S75 and D22S259 was also confirmed in the affected parents and their offspring by dosage analysis. A fluorescence in situ hybridization assay using N-25 YAC and cosmid probes confirmed the presence of a single allele in VCF-10 and VCF-11.

The autosomal dominant inheritance pattern observed in the VCF families in this study is the result of inheritance of a deletion-bearing chromosome rather than a mutation in an autosomal dominantly inherited gene. The results of this study suggest that in most cases VCF is a segmentally aneusomic disorder. However, one of the probands studied (VCF-6) is not deleted at either D22S75 (N25) or D22S259 (pR32). Studies are in progress to determine whether he has a smaller deletion with the DGCR, internal to these two markers. Furthermore, several of his clinical features are atypical for VCF. Therefore, it is possible that this proband does not have VCF.

Molecular of molecular-cytogenetic studies with probes from the DGCR are clearly the most sensitive means of detecting deletions within 22q11. Cytogenetic analysis utilizing high-resolution banding techniques will only detect about 20% of the deletions in this region (VCF-1, VCF-9, VCF-14). Thus, it is believed that cytogenetic analysis is of limited usefulness. Like the detection of deletions in DGS patients, these data support a molecular approach for analysis of patients with VCF. RFLP and DNA dosage studies utilizing probes from the DGCR are useful however, it is believed believe that FISH will be a more rapid and cost efficient method for the detection of deletions.

Seventeen patients with the CHARGE association have also been studied. Fourteen have been studied by dosage with N25 and a deletion has been detected in one patient. This individual is not deleted for R32. All seventeen patients have been studied by dosage with R32 and only a single patient deomonstrated a deletion.

In addition, nine patients with isolated conotruncal cardiac malformations have been studied. Of these patients, four are deleted for N25. Three of these patients are also deleted for R32. These data suggest deletion of overlapping segments of 22q11.2 as genetic etiology for these disorders.

Probes and methods of producing probes directed to the DGCR as well as methods of detecting genetic deletions and mutations associated with DGS, Velocardiofacial syndrome, CHARGE association, conotruncal cardiac defect and cleft palate using probes are provided by the present invention. Kits useful for detection of these genetic deletions and mutations are also provided. The term "mutation" as used herein is meant to refer to a change in the structure of a gene, such as a nucleic acid sequence which varies in as little as one base from the naturally occuring nucleic acid sequence of the gene.

Accordingly, the invention provides methods of detecting deletions and mutations associated with a condition selected from the group consisting of DiGeorge syndrome, Velocardiofacial syndrome, CHARGE association, conotruncal cardiac defects and cleft palate in a human patient. It is believed that Velocardiofacial syndrome, CHARGE association, conotruncal cardiac defects and cleft palate in a human patient are caused by deletions or mutations of a locus or loci in the DiGeorge Syndrome Critical Region. Carey, J. C., *J. Pediatrics*, 96:955–956 (1980); Lammer et al., *Am. J. Med. Genet.*, 2 (suppl.), 113–127 (1986). The methods comprise the step of providing a DNA containing test sample from said human patient. Appropriate test samples such as blood are well known to those in the art. Finally, there is identification of whether there are less than two functional copies of the DiGeorge syndrome critical region loci present in the test sample. Identification can be accomplished in a number of ways such as through the polymerase chain reaction (PCR) or hybridization such as in situ hybridization or restriction fragment length polymorphism (RFLP). PCR is described in U.S. Pat. No. 4,386,202 issued to Mullis which patent is incorporated by reference as if fully set forth herein.

In situ hybridization can be accomplished by contacting a detectably labeled nucleic acid probe, said probe being substantially complementary to unique sequences in the DiGeorge syndrome critical region, with said test sample under hybridizing conditions; and detecting hybridization of said detectably labeled probe with DNA of chromosome 22.

Hybridization of detectably labeled probes and the DGCR occurs under hybridization conditions which will be apparent to those skilled in the art and described in the Examples set forth herein. In one embodiment of the present invention hybridization was performed at 42° C. with 50% formamide, 0.1 X SSC, 0.1% SDS, 3 X SSC, 1% SDS, 5% dextran sulfate, denatured herring sperm DNA (100 μg/ml). In an alternative embodiment of the present invention hybridization may be performed at 65° C. with 1% SDS, 1M NaCl and 10% dextran sulfate.

Detectably labeled probes of the present invention which are substantially complementary to said DGCR will hybridize to said DGCR under hybridizing conditions. The term "substantially complementary" is used herein to describe the commonly understood interaction of complementary base pairing. Imperfect pairing, whether due to deletions or imperfect base matching (i.e. mutation), is envisioned by the present invention when said pairing results in hybridization.

The identification of less than two functional copies of the DiGeorge syndrome critical region loci is indicative of a likelihood that the tested person has a genetic deletion or mutation associated with at least one of DiGeorge syndrome, Velocardiofacial syndrome, CHARGE association, conotruncal cardiac defects and cleft palate.

In another aspect of this invention there is provided a method of preparing diagnostic probes useful for the detection of deletions and mutations associated with a condition selected from the group consisting of DiGeorge Syndrome, Velocardiofacial syndrome, CHARGE association, conotruncal cardiac defects and cleft palate. Primers are prepared which are effective to amplify a region of chromosome 22q11 shown to be unique sequences in the DiGeorge syndrome critical region. DNA is synthesized which is substantially complementary to a region of normal human genomic DNA or cDNA by PCR amplification using pairs of said primers; and a DiGeorge syndrome critical region probe is then isolated from a library containing human chromosome 22 using the substantially complementary DNA.

Conveniently, primers are selected from the group consisting of 5'ACACTGGTCCACAGTGCCAG3' (SEQ ID NO:1) and 5'TGTGAGGGCTTGCTCTGAGC3' (SEQ ID NO:2); 5'TGGTACCGCTGCTCAGAGGGC3' (SEQ ID NO:3) and 5'TCCCAGCCTCTGGCCTGAGTG3' (SEQ ID NO:4); and 5'CTAACACCTATCCTCCGCCG3' (SEQ ID NO:5) and 5'GGCAGCAGGGAAACAGAAAC3' (SEQ ID NO:6).

Alternatively, probes useful for the detection of genetic deletions and mutations associated with a condition selected from the group consisting of DiGeorge Syndrome, Velocardiofacial syndrome, CHARGE association, conotruncal cardiac defects and cleft palate are prepared according to the following steps: PCR amplifying a region of a normal human genomic DNA using the a pair of PCR primers selected from the group consisting of 5'ACACTGGTCCACAGTGCCAG3' (SEQ ID NO:1) and 5'TGTGAGGGCTTGCTCTGAGC3' (SEQ ID NO:2); 5'TGGTACCGCTGCTCAGAGGGC3' (SEQ ID NO;3) and 5'TCCCAGCCTCTGGCCTGAGTG3' (SEQ ID NO:4); and 5'CTAACACCTATCCTCCGCCG3' (SEQ ID NO:5) and 5'GGCAGCAGGGAAACAGAAAC3' (SEQ ID NO:6); and probing a library containing human chromosome 22 sequences with said amplified DNA to isolate a fragment or clone which hybridizes with said amplified DNA.

In another alternative, a diagnostic probe useful for the detection of genetic deletion and mutation associated with a condition selected from the group consisting of DiGeorge syndrome, Velocardiofacial syndrome, CHARGE association, conotruncal cardiac defects, and cleft palate is prepared by PCR amplifying a clone from a library containing chromosome 22 to identify clones containing the probe.

Diagnostic kits for the detection of genetic deletions and mutations associated with a condition selected from the group consisting of DiGeorge syndrome, Velocardiofacial syndrome, CHARGE association, conotruncal cardiac defects and cleft palate comprising a diagnostic probe selected from the group consisting of probes and primers as prepared and described herein.

The following examples are illustrative and are not meant to be limiting of the present invention.

EXAMPLES

EXAMPLE 1

Preparation of Cell Lines

Three cell lines (GM07215, GM07939, GM05876) were obtained from the Coriell Cell Repository (Coriell Institute for Medical Research, Camden, N.J.). Two additional cell lines have been previously described; 7248 (Greenberg et al., (1988), *Am. J. Hum. Genet.* 43: 605–611) and KM4987 (Mascarello et al., (1989), *Am. J. Med. Genet.* 32: 112–114). Patients were obtained from Children's Hospital of Pennsylvania, Philadelphia, Pa. and referring physicians. Blood or skin was obtained to establish lymphoblastoid or fibroblast cell lines. Lymphoblastoid cell lines were established on the parents whenever possible. The analysis includes a total of five DGS families and three VCF families.

EXAMPLE 2

Preparation of Probes

The probes utilized in this study include anonymous markers pH98 (D22S57), pH11 (D22S36), pR32 (D22S259), pH160b (D22S66), pH162 (D22S68) isolated from flow sorted chromosome 22 libraries (Budarf et al., (1991), *Genomics* 3: 168–171). Clone N25 (D22S75) isolated from a NotI linking library (McDermid et al., (1989), *Genomics* 5: 1–8); probe p22/34 (D22S9), isolated from a chromosome 22 enriched library and localized by in situ hybridization to 22q11 (McDermid et al., (1986), *Science* 232:646–648); and probe W21G (D22S24), derived from a flow-sorted chromosome 22 library (Rouleau et al., (1989), *Genomics* 4:1–6) were also used. The probe used for the BCR-related genes is a 160 bp cDNA HindIII/EcoRI fragment from the 3' end of the BCR gene (Budarf et al., (1988), *Genomics* 10:996–1002; Croce et al., (1987) *Proc. Natl. Acad. Sci.* 84: 7174–7178). Probes, βIVS2 and CRI-R365 (D11S129) were used as internal control probes for the dosage studies. Both probes map to chromosome 11 and are not affected by DGS. $\beta IVS_2$ is a 920 bp unique fragment derived from the second intervening sequence of the β-globin gene. CRI-R365 is a unique 2 kb HindIII fragment (Donis-Keller et al., (1987), *Cell* 51: 319–337).

EXAMPLE 3

Clinical and Cytogenetic Studies of DGS patients

Clinical information was obtained either from the referring physicians or from the literature for published cases. High resolution cytogenetic analysis at the 800–850 band stage was performed using standard techniques.

Cytogenetic analysis of the three cell lines obtained from the CCR (Coriell Cell Repository) were initially reported as normal at the 400–450 band stage of resolution. Repeat analysis utilizing high resolution banding techniques demonstrated visible interstitial deletions of 22q11 in GM07215 and GM07939; GM05876 has a possible deletion. Patients 7248, KM4987 and DGS-4 have del 22(q11.21-q11.23). Patients DGS-2 and DGS-3 have possible cytogenetic deletions within 22q11. Patients DGS-1, DGS-5, DGS-6, DGS-7, DGS-8 and DGS-9 have normal karyotypes utilizing high resolution banding techniques. Table 1 summarizes the cytogenetic and clinical findings in the patients.

EXAMPLE 4

DNA Studies of DGS Patients

DNA was extracted from the DGS and parental cell lines by routine methods and was digested with restriction enzymes as recommended by the manufacturer (New England BioLabs). Digested DNA was separated by agarose gel electrophoresis and transferred to either Immobilon (Millipore) or Gene Screen Plus (Dupont) using the method of Southern (Southern, (1975), *J. Mol. Biol.* 98: 503–517). DNA probes were digested with the appropriate restriction enzymes and purified in low melt agarose by gel electrophoresis. DNA probes were labelled with [α-$^{32}$P]dCTP using the random primer method (Feinberg and Vogelstein, (1984), *Anal. Biochem.* 137: 266–267). Labelled probes N25, pR32 and p160b were preannealed with sonicated placental DNA (Litt and White, (1985), *Proc. Natl. Acad. Sci. U.S.A.* 82: 6206–6210). Hybridization was at 42° C. with 50% formamide, 0.1 X SSC, 0.1% SDS, 3 X SSC, 1% SDS, 5% dextran sulfate, denatured herring sperm DNA (100 μg/ml) or at 65° C. with 1% SDS, 1M NaCl and 10% dextran sulfate. Filters were washed twice with 0.2 X SSC, 0.1% SDS at 65° C. and exposed to Kodak XAR-5 film at −70° C. for varying lengths of time.

DNA obtained from cell lines of patients with DGS and their parents was studied by RFLP analysis as described above. Deletions were detected by demonstration of failure to inherit a parental allele. If parental DNA was unavailable, DGS patient cell lines were analyzed for the presence of two alternative alleles. Families who were uninformative using RFLPs and probands demonstrating a single allele at a test locus were subsequently studied with dosage analysis. Probes pH11 (D22S36), N25 (D22S75) and pR32 (D22S259) detected deletions in the five DGS patients for whom parental DNA was available. Deletions were detected in two patients with normal karyotypes, two with visible interstitial deletions and a fifth proband whose cytogenetic study was inconclusive for a deletion.

Probe pR32 (D22S259) was informative in three of five families. This probe detects a 10.1 kb and 9.4 kb allele. Probe pR32 was informative in three families, those of probands 7248, DGS-4 and DGS-5. The father is heterozygous in each family. The mothers of 7248 and cytogenetically normal DGS-5 are homozygous for the 9.4 kb allele. The probands in these two families have a single band, a 10.1 kb allele, inherited from the father. Thus, the child in each of these two families failed to inherit a maternal allele, a 9.4 kb band. The mother of DGS-4 is homozygous for the 10.1 kb allele. The proband has a single 9.4 kb allele shared by the father. This is consistent with a deletion of a maternal allele in these three families. Two of our five DGS families were uninformative at this locus. Nine additional individual DGS probands tested demonstrated a single RFLP allele, consistent with either hemizygosity or dizygosity at this locus. Dosage studies were performed to determine if one or two copies of locus D22S259 were present in these eleven uninformative probands.

Probe N25 (D22S75) was informative in one of five families. One proband with a visible interstitial deletion of 22q11, DGS-4, demonstrated loss of a maternal allele at locus D22S75 (N25) (FIG. 2). The probe N25 detects a TaqI polymorphism, producing alleles of 3.3 or 2.3 and 0.96 kb and a 1.6 kb constant band (Fibison et al., submitted). The father of DGS-4 is homozygous for the 3.3 kb allele; the mother is homozygous for the 2.3 and 0.96 kb allele. Proband DGS-4 has a single band at 3.3 kb, inherited from his father. This is consistent with the loss of the maternal allele at locus D22S259 (pR32) described above for this family. Southern blot analyses of nine individual DGS patients revealed a single allele, again, requiring dosage analysis to determine zygosity.

Two of the five DGS families were informative at locus D22S36 (pH11). RFLP analysis with probe pH11 demonstrated loss of a parental allele in proband DGS-3, who has a possible cytogenetic deletion, and DGS-9, who has a normal karyotype (FIG. 3). Probe pH11 detects a MspI polymorphism which produces two alleles, 3.3 and 1.6 kb, and two constant bands, 3.7 and 2.3 kb. The parents of DGS-3 are homozygous for different alleles. DGS-3 has a 3.3 kb allele shared by his father and he failed to inherit a maternal allele (1.6 kb). The father of the proband DGS-9 is homozygous for the 1.6 kb allele; the mother is heterozygous at this locus. Proband DGS-9 demonstrated a single 3.3 kb allele shared with her mother. She did not inherit a paternal allele. Although nine probands demonstrated single alleles consistent with either hemizygosity or dizygosity at this locus, three probands (KM4987, GM07215, GM07939) were heterozygous. The presence of heterozygous DGS probands excludes locus D22S36 from the minimal critical region.

Table 2 summarizes the results of RFLP analysis of DGS cell lines utilizing eight polymorphic probes previously localized to 22q11. Hemizygous patients are those who failed to inherit a parental allele by RFLP analysis. Eight loci were examined for RFLP status in 5 families. Of the 40 loci tested in the five DGS probands, six deleted loci were ascertained as failure to inherit a parental allele. All deletions were observed at three of the eight loci, D22S36 (pH11), D22S75 (N25) and D22S259 (pR32). Deletions were detected in all five probands using RFLP-based family studies. In addition, nine individual DGS probands were examined for the presence of heterozygosity at these three loci. All of these probands demonstrated a single allele at D22S75 (N25) and D22S259 (pR32) requiring dosage studies. Three probands were heterozygous at D22S36 (pH11), placing D22S36 outside the DGS critical region. RFLP analysis with proximal loci D22S24 (W21G), D22S9 (p22/34) and D22S57 (pH98) and the more distal loci D22S10 (22C1-18) and D22S68 (pH162) failed to detect deletions in the five families studied and thirty to forty percent of the probands tested were heterozygous at these loci. Therefore, based on RFLP analysis proximal loci D22S24, D22S9, D22S57, and D22S36, and distal loci, D22S10 and D22S68 must lie outside the DGS minimal critical region.

EXAMPLE 5

Dosage Analysis of DGS Patients

For cell lines demonstrating a single allele at loci D22S75 (N25) and D22S259 (pR32), Southern blots of HindIII-digested DNA were analyzed by the AMBIS Radioanalytic Imaging System to determine the number of alleles present. Probe N25 detects a 2.6 kb HindIII fragment. The internal control probe, βIVS2 recognizes a distinct 7.8 kb fragment. Southern blot analysis can be used, the intensity of the equivalent hybridization signals for N25 in the two DGS probands is less than that observed in the control when compared with the hybridization signals for βIVS2. Approximately one-half the expected ratio of the counts obtained with N25 to βIVS2 was observed in thirteen of thirteen probands (Table 3). These results are consistent with loss of an allele at locus D22S75 (N25).

Probe pR32 (D22S259) detects an approximately 23 kb Hind III fragment. The ratio of the signal obtained from pR32 to βIVS2 was less than one-half, consistent with the presence of a single allele in the thirteen DGS probands tested (Table 4). Three probands including two of these thirteen (DGS-4, DGS-5) demonstrated loss of a parental allele by RFLP analysis.

Dosage studies were performed with pH160b (D22S66), a nonpolymorphic probe, which has been sublocalized to 22q11 by hybridization to a somatic cell hybrid mapping panel (Budarf et al., (1991), *Genomics* 10: 996–1002). This locus appears to lie between D22S75 (N25) and D22S259 (pR32) (M. Budarf, unpublished results). Probe HI60b recognizes a 2.3 kb HindIII fragment. Loss of an allele was demonstrated in 8 of 8 patients studied (Table 5).

A probe derived from the 3' end of the BCR gene detects four loci: BCR, BCRL2, BCRL3, and BCRL4. These loci map in distinct and separate regions of 22q11 with BCRL2 as the most proximal of these four loci. A HindIII digest produces 23, 19.5, 13 and 9 kb fragments which recognize BCR, BCRL3, BCRL2 and BCRL4, respectively (Croce et al., (1987), *Proc. Natl. Acad. Science, U.S.A.* 84: 7174–7178). Either probe βIVS2 or CRI-R365 which recognizes a 2 kb fragment was used as a control probe. The ratio of the counts obtained from BCRL2 to the control probe was consistent with a deletion of BCRL2 in two DGS cell lines. However, the ratios between the test probe and control probe were similar in seven cell lines (Table 6). Therefore, BCRL2 lies outside the minimal critical region for DGS.

TABLE 1

Summary of Clinical Findings and Cytogenetic Analysis of DGS Patients

| Patient | Heart Defect | Thymic Aplasia[a] or Hypoplasia | Hypocalcemia | Other |
|---|---|---|---|---|
| I. Interstitial del 22(q11.21q11.23) | | | | |
| 7248 | truncus arteriosus, VSD right sided aortic arch | + | + | dysmorphic facies |
| KM4987 | interrupted aortic arch VSD | + | − | dysmorphic facies |
| DGS-4 | tetralogy of Fallot | − | + | |
| GM07215 | interrupted aortic arch ASD, VSD | + | − | |
| GM07939 | truncus arteriosus | +[b] | + | dysmorphic facies |
| II. Possible interstitial deletion | | | | |
| GM05876 | interrupted aortic arch VSD | + | + | dysmorphic facies |
| DGS-2 | VSD | +[b] | + | dysmorphic facies |
| DGS-3 | PDA | +[b] | + | dysmorphic facies |
| III. Normal karyotype | | | | |
| DGS-1 | truncus arteriosus, VSD hypoplastic left heart | + | + | dysmorphic facies biliary cirrhosis abnormally lobed lungs |
| DGS-5 | interrupted aortic arch hypoplastic aorta & valve VSD | + | + | dysmorphic facies |
| DGS-6 | interrupted aortic arch subaortic stenosis, ASD, VSD PDA | +[b] | +[c] | dysmorphic facies |
| DGS-7 | truncus arteriosus right sided aortic arch | + | +[c] | monozygotic twin with double outlet RV, thymic aplasia hypocalcemia |
| DGS-8 | overriding aorta, VSD infundibular stenosis | +[b] | + | dysmorphic facies |
| DGS-9 | interrupted aortic arch VSD | + | + | dysmorphic facies multicystic kidney |

+ and − indicates presence or absence of clinical feature, respectively;
[a]includes radiographic absence of thymic shadow, absent or small thymus at surgery or autopsy;
[b]documented cellular immune deficiency;
[c]transient decrease in serum calium

TABLE 2

Summary of RFLP Status or DGS Cell Lines Studied with Polymorphic Probes

| | probes | | | | | | | |
|---|---|---|---|---|---|---|---|---|
| | W21G | p22/34 | pH98 | pH11 | N25 | pR32 | 22C1-18 | pH162 |
| Hemizygous[a] | 0 | 0 | 0 | 2 | 1 | 3 | 0 | 0 |
| Heterozygous[b] | 5 | 5 | 2 | 3 | 0 | 0 | 5 | 4 |
| Uninformative[c] | 1 | 8 | 5 | 9 | 13 | 11 | 7 | 3 |
| Total cell lines studied | 6 | 13 | 7 | 14 | 14 | 14 | 12 | 7 |

[a]Hemizygous indicates numer of probands demonstrating failure to inherit a parental allele (five families studied).
[b]Heterozygous indicates probands with two different alleles.
[c]Uninformative indicates probands with a single band which may be consistent with one or two alleles, requiring dosage analysis.

TABLE 3

Dosage Analysis: D22S75 (N25)

| Patient | Ratio of N25/βIVS$_2$ | | | | |
|---|---|---|---|---|---|
| | 1 | 2 | 3 | Avg | # Alleles |
| control | 1.8 | 2.0 | 2.2 | 2.0 | 2.0 |
| GM07215 | 1.2 | 0.7 | 0.9 | 0.9 | 1.0 |
| GM07939 | 1.1 | 1.0 | 1.3 | 1.1 | 1.1 |
| KM4987 | 1.0 | 1.2 | 1.2 | 1.1 | 1.1 |
| control | 15.9 | 16.8 | 15.0 | 15.9 | 2.0 |
| DGS-3 | 7.9 | 7.7 | 6.9 | 7.5 | 0.9 |
| DGS-4 | 7.4 | 6.2 | 9.3 | 7.6 | 1.0 |
| DGS-5 | 7.9 | 8.0 | 8.4 | 8.1 | 1.0 |
| control | 8.8 | 8.2 | 9.0 | 8.7 | 2.0 |
| GM05876 | 5.2 | 5.1 | 4.7 | 5.0 | 1.1 |
| DGS-1 | 6.1 | 6.4 | 4.6 | 5.7 | 1.3 |
| DGS-2 | 5.7 | 4.8 | 4.9 | 5.1 | 1.2 |
| DGS-7 | 6.0 | 5.1 | 5.2 | 5.4 | 1.2 |
| control | 18.3 | 20.7 | 20.1 | 19.7 | 2.0 |
| DGS-6 | 5.1 | 6.2 | 8.8 | 6.7 | 0.7 |
| DGS-8 | 5.2 | 7.8 | 8.0 | 7.0 | 0.7 |
| DGS-9 | 7.1 | 8.5 | 7.5 | 7.7 | 0.8 |

TABLE 4

Dosage Analysis: D22S259 (pR32)

| Patient | Ratio of R32/βIVS$_2$ | | | | |
|---|---|---|---|---|---|
| | 1 | 2 | 3 | Avg | # Alleles |
| control | 2.1 | 3.0 | 2.7 | 2.6 | 2 |
| GM07215 | 0.7 | 1.1 | 1.5 | 1.1 | 0.8 |
| GM07939 | 1.3 | 1.1 | 0.7 | 1.0 | 0.8 |
| GM05876 | 0.9 | 1.9 | 0.9 | 1.2 | 0.9 |
| KM4987 | 1.2 | — | 1.0 | 1.1 | 0.8 |
| control | 5.3 | 4.1 | 8.2 | 5.9 | 2 |
| DGS-6 | 1.2 | 2.7 | 0.9 | 1.6 | 0.5 |
| DGS-8 | 1.4 | 1.7 | 2.2 | 1.8 | 0.6 |
| DGS-9 | 2.3 | 1.0 | 1.7 | 1.7 | 0.6 |
| control | 3.9 | 3.0 | 3.6 | 3.5 | 2 |
| DGS-1 | 1.8 | 1.2 | 1.2 | 1.4 | 0.8 |
| DGS-2 | 1.7 | 1.8 | 1.5 | 1.7 | 1.0 |
| DGS-7 | 1.1 | 1.1 | 1.3 | 1.2 | 0.7 |
| control | 4.4 | 4.5 | 4.7 | 4.5 | 2 |
| DGS-3 | 2.6 | 1.8 | — | 2.2 | 1.0 |
| DGS-4 | 1.5 | 0.8 | — | 1.2 | 0.5 |
| DGS-5 | 1.4 | 1.3 | — | 1.4 | 0.6 |

TABLE 5

Dosage Analysis: D22S66 (pH160b)

| Patient | Ratio of H160b/βIVS$_2$ | | | | |
|---|---|---|---|---|---|
| | 1 | 2 | 3 | Avg | # Alleles |
| control | 1.3 | 1.3 | 1.1 | 1.2 | 2 |
| GM05876 | 0.5 | 0.5 | 0.3 | 0.4 | 0.7 |
| DGS-1 | 0.7 | 0.6 | 0.5 | 0.6 | 1.0 |
| DGS-2 | 0.3 | 0.4 | 0.6 | 0.4 | 0.7 |
| DGS-7 | 0.8 | 0.3 | 0.7 | 0.6 | 1.0 |
| control | 1.6 | 1.6 | — | 1.6 | 2 |
| KM4987 | 0.7 | 0.5 | 0.7 | 0.6 | 0.8 |
| DGS-3 | 0.8 | 0.6 | 0.4 | 0.6 | 0.8 |
| DGS-4 | — | 0.7 | 0.6 | 0.7 | 0.9 |
| DGS-5 | 0.3 | 0.9 | 0.5 | 0.6 | 0.8 |

TABLE 6

Dosage Analysis: BCRL2

| Patient | 1 | 2 | 3 | Avg | # Alleles |
|---|---|---|---|---|---|
| | Ratio of BCRL2/βIVS$_2$ | | | | |
| control | 0.49 | 0.55 | 0.46 | 0.50 | 2 |
| DGS-6 | 0.21 | 0.17 | 0.21 | 0.20 | 0.8 |
| DGS-8 | 0.22 | 0.31 | 0.24 | 0.26 | 1.0 |
| DGS-9 | 0.38 | 0.63 | 0.48 | 0.50 | 2 |
| control | 0.31 | 0.38 | 0.43 | 0.37 | 2 |
| DGS-4 | 0.43 | 0.24 | 0.46 | 0.38 | 2 |
| 7248 | 0.46 | 0.38 | 0.53 | 0.46 | 2.4 |
| | Ratio of BCRL2/CRI-R365 | | | | |
| control | 0.62 | 0.56 | 0.65 | 0.61 | 2 |
| GM07215 | 0.48 | 0.55 | 0.48 | 0.50 | 1.7 |
| GM07939 | 0.49 | 0.54 | 0.51 | 0.52 | 1.7 |
| KM4987 | 0.48 | 0.55 | 0.59 | 0.54 | 1.8 |
| GM05876 | 0.51 | 0.46 | 0.56 | 0.51 | 1.7 |

EXAMPLE 6

Clinical and Cytogenetic Studies of VCF Patients

Fifteen patients including two affected mothers and their affected daughters were referred with the diagnosis of VCF. Cytogenetic analysis of metaphase chromosomes was performed at the 800–850 band level of resolution using standard techniques. Table 8 summarizes the clinical features of the VCF patient studies.

TABLE 8

Summary of Clinical Findings of VCF Patients

| Patient | Palatal Abnormality | Cardiac Defect | Learning Disability | Typical Facies | Other |
|---|---|---|---|---|---|
| VCF-1 | + | — | + | + | |
| VCF-2 | −[c] | — | + | + | |
| VCF-3 | + | — | + | + | parent of 3 affected offspring[d] |
| VCF-4 | + | PDA | + | + | growth retardation, hypothyroidism, inguinal hernia, retinal vessel tortuosity, 2-3 syndactyly |
| VCF-5[a] | + | VSD | + | + | retinal vessel tortuosity, exotropia, 2-3 syndactyly |
| VCF-6 | + | perimembranous VSD | + | + | growth retardation, hypospadias |
| VCF-7 | + | VSD, rt. aortic arch | + | + | |
| VCF-8 | + | Rt. aortic arch | + | + | |
| VCF-9 | + | TOF, rt. | + | + | microcephaly, |

TABLE 8-continued

Summary of Clinical Findings of VCF Patients

| Patient | Palatal Abnormality | Cardiac Defect | Learning Disability | Typical Facies | Other |
|---|---|---|---|---|---|
| VCF-10[b] | + | aortic arch | + | + | brachydactyly |
| VCF-11 | + | — | + | + | |
| VCF-12 | + | — | + | + | retinal vessel tortuosity |
| VCF-13 | + | VSD coarctation of aorta | + | + | |
| VCF-14 | + | VSD coarctation of aorta | + | + | laryngeal web, psychiatric illness |
| VCF-15 | + | — | + | + | growth retardation, hypocalcemia |

(+) indicates presence of clinical feature;
(−) indicates absence of clinical feature.
VSD = ventricular septal defect; TOF = tetralogy of Fallot;
[a]Mother of VCF-4;
[b]Mother of VCF-11;
[c]hypernsal speech;
[d]offspring have not been studied.

All of the patients have the characteristic facial features described by Shprintzen et al. (1978), *Cleft Palate J.* 15: 56 and Shprintzen, et al. (1981), *Pediatr.* 67: 167–172 and learning disabilities. However, in addition to a cleft palate, perimembranous VSD and hypospadias, patient VCF-6 appears to have a more severe degree of developmental delay and growth retardation than previously reported in VCF. Fourteen patients have palatal abnormalities including cleft palate and velo-pharyngeal insufficiency. The remaining patient (VCF-2) has hypernasal speech. Cardiac defects were found in 8 of 15 patients.

Three of 15 patients (VCF-1, VCF-9, VCF-14) have interstitial deletions of 22q11 [del(22)(q11.21q11.23)]. The remaining 12 patients have normal karyotypes using high-resolution banding techniques (800–850 band level of resolution).

EXAMPLE 7

DNA Studies of VCF Patients

DNA obtained from cell lines of 15 patients with VCF and their parents, when available, was studies by RFLP analysis with probes N25 (D22S75) and pR32 (D22S259). Deletions were detected in three patients with normal karyotypes by demonstration of failure to inherit a parental allele either at locus D22S259 or D22S75. An autoradiogram of two Southern blots of genomic DNA digested with TaqI and probed with pR32 (D22S259) shows that the probe detects either a 10.1 or a 9.4 kb allele. The unaffected parents are homozygous for alternate alleles. The proband (VCF-8) has a single allele shared by here mother; she failed to inherit a paternal allele. In another case the mother (VCF-5) has a 10.1-kb allele while here daughter (VCF-4) has a 9.4-kb allele. Thus, VCF-4 did not inherit a maternal 10.1-kb allele. One family (VCF-10, VCF-11) was informative at locus D22S75 (N25). Proband VCF-11 and her affected mother (VCF-10) do not share the same band therefore, VCF-10 did not inherit a maternal allele. The remaining 11 probands studied demonstrated a single band at both loci D22S75 and D22S259. This is consistent with either 1 or 2 copies of the locus (hemi- or homozygosity, respectively) and required dosage analysis to determine the number of alleles present.

EXAMPLE 8

Dosage Analysis of VCF Patients

All of the VCF patients including patients shown to be deleted by RFLP analysis were analyzed for copy number at loci D22S75 (N25) and D22S259 (pR32). Southern blots of restriction enzyme digested DNA were analyzed by the AMBIS Radioanalytic Imaging System to determine the number of alleles present. The results of these quantitation experiments are summarized in Table 9.

TABLE 9

Summary of Dosage Analysis of VCF Cell Lines by Quantitative Hybridization

| Patient | Probe | |
|---|---|---|
| | N25 | pR32 |
| VCF-1 | 1.00 | 1.04 |
| VCF-2 | 0.57 | 0.73 |
| VCF-3 | 1.06[b] | 0.90 |
| VCF-4 | 0.82 | 0.59[a] |
| VCF-5 | 0.41 | 0.80 |
| VCF-6 | 1.99 | 2.01 |
| VCF-7 | 1.19 | 0.98 |
| VCF-8 | 1.08[b] | 0.76[a] |
| VCF-9 | 1.12 | 1.29 |
| VCF-10 | 1.02[b] | 0.66 |
| VCF-11 | 0.82[a,b] | 0.96 |
| VCF-12 | 1.23 | 1.01 |
| VCF-13 | 1.11 | 1.08 |
| VCF-14 | 1.04 | 0.91 |
| VCF-15 | 1.09 | 1.05 |

[a]Copy number was also demonstrated by RFLP analysis.
[b]Copy number was confirmed by fluorescence in situ hybridization with N25 YAC and cosmid clones.

The values of Table 9 represent locus copy number, standardized from quantitative analysis of the hybridization signals obtained with the test probe relative to those obtained with a control probe. They were obtained by taking the mean of three independent ratios of patient to control. Values less than 1.50 are consistent with a deletion. Fourteen of 15 patients were hemizygous at both loci. A deletion at either locus was not detected in one patient (VCF-6).

What is claimed is:

1. A method of detecting genetic deletions and mutations associated with at least one condition selected from the group consisting of DiGeorge syndrome, Velocardiofacial syndrome, CHARGE association, conotruncal defect and cleft palate in a human patient comprising the steps of:

isolating a diagnostic probe by PCR amplifying a region of normal human genomic DNA using a pair of PCR primers having sequences selected from the group consisting of: 5'ACACTGGTCCACAGTGCCAG3' (SEQ ID NO:1) and 5'TGTGAGGGCTTGCTCTGAGC3' (SEQ ID NO:2); 5'TGGTACCGCTGCTCAGAGGGC3' (SEQ ID NO:3) and 5'TCCCAGCCTCTGGCCTGAGTG3' (SEQ ID NO:4); and 5'CTAACACCTATCCTCCGCCG3' (SEQ ID NO:5) and 5'GGCAGCAGGGAAACAGAAAC3' (SEQ ID NO:6);

probing a library containing human chromosome 22 sequences with said amplified DNA to isolate a probe which hybridizes with said amplified DNA;

detectably labeling said diagnostic probe;

providing a DNA containing test sample from said patient;

contacting the detectably labeled diagnostic probe with DNA from said test sample under hybridization conditions; and     detecting hybridization of said detectably labeled diagnostic probe with said DNA from said test sample,     whereby the absence of hybridization of said detectably labeled diagnostic probe is diagnostic of the likelihood said human has a deletion or mutation associated with at least one of DiGeorge syndrome, Velocardiofacial syndrome, CHARGE association, conotruncal cardiac defect and cleft palate.

2. A diagnostic probe useful for the detection of genetic deletions and mutations associated with at least one condition selected from the group consisting of DiGeorge Syndrome, Velocardiofacial syndrome, CHARGE association, conotruncal cardiac defect and cleft palate isolated according to the following steps:

PCR amplifying a region of a normal human genomic DNA using a pair of PCR primers having sequences selected from the group consisting of 5'ACACTGGTCCACAGTGCCAG3' (SEQ ID NO:1) and 5'TGTGAGGGCTTGCTCTGAGC3' (SEQ ID NO:2); 5'TGGTACCGCTGCTCAGAGGGC3' (SEQ ID NO:3) and 5'TCCCAGCCTCTGGCCTGAGTG3' (SEQ ID NO:4); and 5'CTAACACCTATCCTCCGCCG3' (SEQ ID NO:5) and 5'GGCAGCAGGGAAACAGAAAC3' (SEQ ID NO:6) and     probing a library containing human chromosome 22 sequences with said amplified DNA to isolate a probe which hybridizes with said amplified DNA.

3. A diagnostic kit for the detection of genetic deletions and mutations associated with at least one condition selected from the group consisting of DiGeorge syndrome, Velocardiofacial syndrome, CHARGE association, conotruncal cardiac defect and cleft palate comprising primer pairs wherein the primer pairs have sequences selected from the group consisting of 5'ACACTGGTCCACAGTGCCAG3' (SEQ ID NO:1) and 5'TGTGAGGGCTTGCTCTGAGC3' (SEQ ID NO:2); 5'TGGTACCGCTGCTCAGAGGGC3' (SEQ ID NO:3) and 5'TCCCAGCCTCTGGCCTGAGTG3' (SEQ ID NO:4); and 5'CTAACACCTATCCTCCGCCG3' (SEQ ID NO:5) and 5'GGCAGCAGGGAAACAGAAAC3' (SEQ ID NO:6).

4. A method of detecting genetic deletions and mutations associated with at least one condition selected from the group consisting of DiGeorge syndrome, Velocardiofacial syndrome, CHARGE association, conotruncal defect and cleft palate in a human patient comprising the steps of:

isolating a diagnostic probe by PCR amplifying a region of normal human genomic DNA using a pair of PCR primers having the sequences 5'ACACTGGTCCACAGTGCCAG3' (SEQ ID NO:1) and 5'TGTGAGGGCTTGCTCTGAGC3' (SEQ ID NO:2) and     probing a library containing human chromosome 22 sequences with said amplified DNA to isolate a probe which hybridizes with said amplified DNA;

detectable labeling said diagnostic probe;

providing a DNA containing test sample from said patient;

contacting said detectably labeled diagnostic probe with DNA from said test sample under hybridization conditions; and     detecting hybridization of said detectably labeled probe with said DNA from said test sample,     whereby the absence of hybridization of said detectably labeled probe is diagnostic of the likelihood said human has a deletion or mutation associated with at least one of DiGeorge syndrome, Velocardiofacial syndrome, CHARGE association, conotruncal cardiac defect and cleft palate.

5. A diagnostic probe useful for the detection of genetic deletions and mutations associated with at least one condition selected from the group consisting of DiGeorge Syndrome, Velocardiofacial syndrome, CHARGE association, conotruncal cardiac defect and cleft palate prepared according to the following steps:

PCR amplifying a region of normal human genomic DNA using a pair of PCR primers having the sequences 5'ACACTGGTCCACAGTGCCAG3' (SEQ ID NO:1) and 5'TGTGAGGGCTTGCTCTGAGC3' (SEQ ID NO:2) and probing a library containing human chromosome 22 sequences with said amplified DNA to isolate a fragment or clone which hybridizes with said amplified DNA.

6. A diagnostic kit for the detection of genetic deletions and mutations associated with at least one condition selected from the group consisting of DiGeorge syndrome, Velocardiofacial syndrome, CHARGE association, conotruncal cardiac defect and cleft palate comprising a pair of PCR primers having the sequences 5'ACACTGGTCCACAGTGCCAG3' (SEQ ID NO:1) and 5'TGTGAGGGCTTGCTCTGAGC3' (SEQ ID NO:2).

* * * * *

UNITED STATES PATENT AND TRADEMARK OFFICE
CERTIFICATE OF CORRECTION

PATENT NO. : 5,576,178
DATED : November 19, 1996
INVENTOR(S) : Emanuel et al.

It is certified that error appears in the above-identified patent and that said Letters Patent is hereby corrected as shown below:

Col. 2, line 2, please delete "possible" and insert therefor --possibly--.
Col. 4, line 12, please insert --of-- between "detection" and "genetic".
Col. 8, line 5, please delete the word "believe".
Col. 17, line 57, please delete "here" and insert therefor --her--.

Signed and Sealed this

Eighth Day of December, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

ACACTGGTCC ACAGTGCCAG                                                     20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

TGTGAGGGCT TGCTCTGAGC                                                     20

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

TGGTACCGCT GCTCAGAGGG C                                                21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

TCCCAGCCTC TGGCCTGAGT G                                                21

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:5:

```
CTAACACCTA TCCTCCGCCG                                                           20
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:6:

```
GGCAGCAGGG AAACAGAAAC                                                           20
```